(12) United States Patent
Infante et al.

(10) Patent No.: US 9,486,516 B2
(45) Date of Patent: Nov. 8, 2016

(54) FORMULATIONS FOR NON-INVASIVE DELIVERY OF ACTIVE PROTEINS TO AN ANIMAL OR HUMAN

(75) Inventors: Victor Infante, El Puerto de Santa Maria (ES); Juan Jose Infante, Dos Hermanas (ES); Kevin O'Connor, Dos Hermanas (ES); David Cotan, Olivares (ES)

(73) Assignee: BIOORGANIC RESEARCH AND SERVICES SA, Jerez de la Frontera (ES)

(*) Notice: Subject to any disclaimer, the term of this patent is extended or adjusted under 35 U.S.C. 154(b) by 0 days.

(21) Appl. No.: 14/386,758

(22) PCT Filed: Mar. 22, 2012

(86) PCT No.: PCT/EP2012/055069
§ 371 (c)(1),
(2), (4) Date: Sep. 19, 2014

(87) PCT Pub. No.: WO2013/139393
PCT Pub. Date: Sep. 26, 2013

(65) Prior Publication Data
US 2015/0273050 A1 Oct. 1, 2015

(51) Int. Cl.
*C07K 14/435* (2006.01)
*A61K 39/205* (2006.01)
*A61K 39/00* (2006.01)
(Continued)

(52) U.S. Cl.
CPC ............. *A61K 39/205* (2013.01); *A61K 39/00* (2013.01); *A61K 39/12* (2013.01); *C07K 14/005* (2013.01); *C07K 14/43586* (2013.01); *C12N 7/00* (2013.01); *A61K 2039/5256* (2013.01); *A61K 2039/542* (2013.01); *A61K 2039/552* (2013.01); *A61K 2039/6031* (2013.01); *C07K 2319/40* (2013.01); *C12N 2710/14043* (2013.01);
(Continued)

(58) Field of Classification Search
CPC ............... A61K 2039/552; A61K 2039/6031; A61K 39/00; A61K 39/12; C07K 2319/00; C07K 14/005; C12N 9/93; C12N 2710/14043; C12N 2760/20034; C12P 7/6463
See application file for complete search history.

(56) References Cited

FOREIGN PATENT DOCUMENTS

EP 2105129 A2 9/2009
WO WO 2011/082087 A2 7/2011
(Continued)

OTHER PUBLICATIONS

Arrese et al. (1) Archived of Biochemistry and Biophysics, 2008, vol. 473, Issue 1, pp. 42-47.*
(Continued)

*Primary Examiner* — Bao Li
(74) *Attorney, Agent, or Firm* — DLA Piper LLP (US)

(57) ABSTRACT

This invention relates to formulations which contain at least one active peptide intended to be used for prevention or treatment of a condition in an animal or human. Said active peptide has been expressed in a system that improves the conservation of those properties essential to the prophylactic or therapeutic effect of said peptide before and after delivery to an animal or human and until the peptide delivers its activity at the effector site within said animal or human. The invention is particularly relevant to formulations of oral or mucosal vaccines or biopharmaceuticals. The active peptide of the formulation is recombinantly expressed in cells or whole animals. In a preferred embodiment of this invention the active polypeptide of the formulation has been recombinantly expressed in insect cells or whole insect larvae.

9 Claims, 1 Drawing Sheet

(51) Int. Cl.
*A61K 39/12* (2006.01)
*C07K 14/005* (2006.01)
*C12N 7/00* (2006.01)

(52) U.S. Cl.
CPC ............... *C12N2760/20034* (2013.01); *C12N 2760/20071* (2013.01)

(56) References Cited

FOREIGN PATENT DOCUMENTS

WO    WO 2011/147995 A1    12/2011
WO    WO 2011147995 A1 *   12/2011

OTHER PUBLICATIONS

Arrese et al. (2) Insect Biochemistry and Molecular Biology, 2008, vol. 38, pp. 993-1000.*
Burke et al. J. Virol. 86 (6), 3293-3306 (2012.*
Ohnishi et al. The Journal of Biological Chemistry, Jul. 2011vol. 286, No. 27, pp. 24101-24112.*
Pan et al. Journal of Protein Chemistry, 1999, vol. 18, No. 5, pp. 579-584.*
Miki et al. Journal of Biological Chemistry, 1999, vol. 274, No. 41, pp. 29057-29062.*
Black et al. Journal of Biological Chemistry, 1992, vol. 267, No. 14, pp. 9743-9748.*
Kumar Shantanu et al, "Tomato bushy stunt virus (TBSV), a versatile platform for polyvalent display of antigenic . . . " by in Virology, vol. 388, No. 1, May 2009, pp. 185-190.
Takamasa Inoue et al, "Engineering of SV40-based nano-capsules for delivery of heterologous . . . " in Journal of Biotechnology, vol. 134, No. 1-2, Jan. 3, 2008, pp. 181-192.
Zahohui Gong et al, "Suppression of diabetes in non-obese diabetic (NOD) mice by oral . . . " in Vaccine, Elsevier Ltd, Great Britain, vol. 25, No. 8, Jan. 23, 2007, pp. 1444-1451.
Anne Garcia et al, "The Central Domain Is Required to Target and Anchor Perilipin A to . . . " in Journal of Biological Chemistry, vol. 278, No. 1, Dec. 27, 2002, pp. 625-635.
Jan Holmgren et al, "Mucosal immunity and vaccines" in Nature Medicine, 2005, vol. 4, pp. 45-53.
Stephen J. Streatfield, "Mucosal immunization using recombinant plant-based oral vaccines" in Methds, 2006, vol. 38, pp. 150-157.
Suresh P Vyas et al, "Implication of nanoparticles/microparticles in mucosal vaccine delivery" in Expert Rev. Vaccines, 2007, vol. 6, pp. 401-418.
Mark A. Jepson et al,"M cell targeting by lectins: a strategy for mucosal vaccination and drug delivery" in Advanced Drug Delivery Reviews, 2004, vol. 56, No. 4, pp. 511-525.
Hai-Long Xiao et al, "Oral administration activity determination of recombinant osteoprotegerin from . . . " in Molecular Biotechnology, 2007, vol. 35, No. 8, pp. 179-184.
Archana Monie et al, "Cervarix: a vaccine for the prevention of HPV 16, 18-associated cervical cancer" in Biologics: Targets & Therapy, 2008, vol. 2, No. 1, pp. 107-113.
Llorenc Grau-Roma et al, "Recent advances in the epidemiology, diagnosis and control of diseases caused by . . . " in the Veterinary Journal, 2011, vol. 187, No. 1, pp. 23-32.
Sandra Hervas-Stubbs et al, "Insect baculoviruses strongly potentiate adaptive immune responses by . . . " in The Journal of Immunology, 2007, vol. 178, No. 4, pp. 2361-2369.

* cited by examiner

FORMULATIONS FOR NON-INVASIVE DELIVERY OF ACTIVE PROTEINS TO AN ANIMAL OR HUMAN

FIELD OF INVENTION

The present invention relates to a formulation comprising a pharmaceutically active agent, such as, but not limited to, an immunogenic agent (e.g., a vaccine). Said formulation is prepared by heterologous expression of a fusion peptide in host cells or organisms. The sequence of the fusion peptide leads to the assembly of the active agent into stable nanostructures, which allow administration and delivery of an effective amount of unaltered pharmaceutically active agent to the effector site in an animal or human. In a preferred embodiment of this invention the formulation is prepared by homogenization of lepidopteran larvae used for heterologous expression of said fusion peptide and is intended for delivery to an animal by the oral route.

BACKGROUND OF ART

The induction of mucosal immunity is very important in conferring protection against pathogens that typically invade via mucosal surfaces. Delivery of a vaccine to a mucosal surface optimizes the induction of mucosal immunity. The apparent linked nature of the mucosal immune system allows delivery to any mucosal surface to potentially induce immunity at others HOLMGREM, J, et al. Mucosal immunity and vaccines. *Nat. Med.* 2005, vol. 4, p. S45-53. Oral administration is a very straightforward and inexpensive approach to deliver a vaccine to the mucosal lining of the gut. However, vaccines administered by this route are subject to proteolysis in the gastrointestinal tract. Thus, dose levels for protein subunit vaccines are likely to be very high and the antigen may need to be protected from proteolysis for oral delivery to be efficacious STREATFIELD, S. J., et al. Mucosal immunization using recombinant plant-based oral vaccines. *Methods.* 2006, vol. 38, no. 2, p. 150-157.

As a consequence, orally delivered bacterin or subunit vaccines have not been proven to be efficacious since the antigens are generally modified by the stomach prior to presentation to the immune-responsive cells of the gut mucosa. A number of approaches have been tested to provide an oral delivery vehicle that would transit the stomach but most have been unsuccessful at the commercial scale.

Polymeric nanoparticles/microparticles have been proposed as a solution for the mucosal administration of conventional drugs. However they have not yet been developed commercially for vaccine delivery, although several polymeric delivery systems for mucosal vaccine delivery are currently being evaluated. The polymer-based approaches are designed to protect the antigen in the gut, to target the antigen to the gut-associated lymphoid tissue or to increase the residence time of the antigen in the gut through bioadhesion VYAS, S. P., et al. Implication of nanoparticles/microparticles in mucosal vaccine delivery. *EXPERT REV. VACCINES.* 2007, vol. 6, no. 3, p. 401-18. However, many hurdles must be overcome before these approaches become a practical reality. Among them, the use of organic solvents and materials for preparation of the particles can pose a threat to the vaccinated organism or the environment EP 2105129 A (HAREL)) In addition, preparation of the particles often increase the production cost to levels unaccepted for their use especially in the veterinary sector.

Since oral administration of protein subunit vaccines has to face proteolysis in the gastrointestinal tract, the dose levels for protein subunit vaccines are likely to be very high and the antigen may need to be protected from proteolysis for oral delivery to be efficacious. Obtaining a relatively high amount of antigen is both difficult and expensive if classical cell culture-based recombinant expression platforms are used. On the other hand, once an effective amount of unaltered antigen has reached the gut mucosa, the antigen must be targeted to the mucosal cells specialized in triggering the immune response JEPSON, M. A., et al. M cell targeting by lectins: a strategy for mucosal vaccination and drug delivery. *Adv. Drug. Deliv. Rev.* 2004, vol. 56, no. 4, p. 511-25.

The search for inexpensive production systems capable of producing large quantities of recombinant protein has resulted in the development of new technology platforms. The lepidopteran larvae-based baculovirus expression system is an inexpensive and high level expression system. An interesting aspect of this technology is sustained by different experiments showing that administration of either vaccines or biopharmaceuticals in crude purified extracts of lepidopteran larvae by the oral route to mice led to absorption by the mucosa at different levels, producing systemic activity of the active compound GONG, Z. Suppression of diabetes in non-obese diabetic (NOD) mice by oral administration of a cholera toxin B subunit-insulin B chain fusion protein vaccine produced in silkworm. *vaccine.* 2007, vol. 25, no. 8, p. 1444-51. XIAO, H. L., et al. Oral administration activity determination of recombinant osteoprotegerin from silkworm larvae. *Molecular Biotechnology.* 2007, vol. 35, no. 8, p. 179-84.

The baculovirus expression technology is widely used for production of recombinant vaccines based on virus-like particles (VLPs) or glycosylated viral antigens, both for human and veterinary use. Some of these products are on the market. Examples are the human papillomavirus vaccine Cervarix® commercialized by GSK MONIE, A., et al. Cervarix: a vaccine for the prevention of HPV 16, 18-associated cervical cancer. *Biologics.* 2008, vol. 2, no. 1, p. 97-105. or the protective vaccines against Porcine Circovirus 2 marketed by Intervet (Merck Animal Health)—Circumvent PCV® and Porcilis PCV® GRAU-ROMA, L., et al. Recent advances in the epidemiology, diagnosis and control of diseases caused by porcine circovirus type 2. *Vet. J.* 2011, vol. 187, no. 1, p. 23-32.

Different authors have shown that VLPs produced by the baculovirus expression technology are highly efficient vehicles for delivering heterologous cytotoxic T lymphocytes epitopes to the MHC-I pathway because they can induce potent immune responses in the absence of exogenous adjuvants. Although these immunostimulatory properties were first completely attributed to the particulate structure of the VLPs, it has been shown that the adjuvant effect of these particles is dependent on the presence of active BVs HERVAS-STUBBS, S., et al. Insect baculoviruses strongly potentiate adaptive immune responses by inducing type I IFN. *J. Immunol.* 2007, vol. 178, no. 4, p. 2361-69. which are concomitant to the production process, making antigens expressed by baculovirus unique vaccine candidate products.

The present invention relates to solve technological, environmental, and economical problems that currently hamper development and marketing of vaccines or biopharmaceuticals.

SUMMARY OF THE INVENTION

In the present invention, the active agents are obtained by recombinant expression of fusion peptides. The expression leads to accumulation of the active agents within the host cells, the culture media, or the body of the host organism, either attached to lipid membranes or aggregated in the form of stable particles. The active agent is a fusion peptide formed by two sequences linked together, in which one of the sequences is a product of interest and the other promotes either the fusion of the product of interest to lipid membranes or accumulation of the product of interest into stable particles. The product of interest can be selected from, but it is not restricted to, immunogenic peptides and proteins able to induce an immune response in an animal or human against pathogens. In addition, the product of interest can be selected from, but it is not restricted to, peptides and proteins with a therapeutic effect on the condition of an animal or human.

In an aspect of the present invention the active agents are peptides expressed fused to sequences that promotes attachment to lipid droplets or lipid membranes in general. Attachment to lipid membranes promotes natural encapsulation of the active agent into liposomes when the host cells or host organisms are processed to recover said active agent. Further description of the sequences used for attachment of the active agent to lipid membranes is provided below.

In another aspect of the present invention the active agents are peptides expressed fused to sequences that promotes aggregation of said active agents into stable protein particles. The particulate nature of these structures promotes stability of the active agent by preventing degradation by proteases and facilitates recognition of the active agent by the immune-responsive cells of the mucosa. Further description of the sequences used for inducing aggregation of the active agent into protein particles is provided below.

In a further aspect of the present invention, fusion to lipid membranes or aggregation into protein particles are used to develop specific purification methods of the active agents.

In a preferred embodiment of the present invention the fusion peptides are expressed in insect larvae by using the baculovirus expression vector technology KATO, T., et al. Silkworm expression system as a platform technology in life science. *Appl. Microblol. Biotechnol.* 2010, vol. 85, no. 3, p. 1459-70. COX, M. M., et al. Recombinant protein vaccines produced in insect cells. *Vaccine.* 2012, vol. 30, no. 10, p. 1759-66.

The present invention provides a method of obtaining a formulation of naturally encapsulated bioactive peptides based on the heterologous expression of the fusion peptides described above. Said method comprises:

1. growing host cells or host organisms under conditions that allow expression of the heterologous peptides consisting in the fusion of a product of interest to a sequence that promotes either attachment to lipid membranes or aggregation into stable protein particles,
2. harvesting said host cells or host organisms, or taking a sample from the host cells culture media or from the body of said organism and, if desired,
3. preparing a clarified homogenate or crude extract, and, if desired,
4. enriching the level of purity of said heterologous peptide in the homogenate or crude extract, and, if desired adding a substance that modifies the physicochemical properties of the final formulation.

In a preferred embodiment of the present invention, said formulation is prepared by homogenization of insect larvae, which were infected with at least one recombinant baculovirus expressing the fusion peptide. Homogenized insect larvae in which the fusion peptide accumulated by using the baculovirus expression vector technology provides a cost-effective and natural formulation for oral or mucosal delivery of vaccines or biopharmaceuticals.

In another aspect of the present invention, the formulation obtained by heterologous expression of the fusion peptides is used for oral or mucosal vaccination of an animal or human. In a preferred embodiment of this invention the vaccinated animal is selected from the group of fishes, crustaceans, birds, or cattle. In a more preferred embodiment the animals are fed with the formulation.

In a still further aspect of the present invention, the formulation obtained by heterologous expression of the fusion peptides is used for intestinal delivery of a pharmaceutically active agent to an animal or human. In a preferred embodiment of this invention the formulation is used to feed humans and intended to deliver an active agent to the intestinal mucosa. In a more preferred embodiment the active agent is a lysosomal enzyme used to treat a lysosomal storage disorder.

In a more specific aspect of the present invention the fusion peptide is a glycopeptide. If the glycopeptide is recombinantly expressed in the preferred insect host, the glycopeptide is known to present a high level of terminal mannose residues exposed. These residues specifically interact with mannose receptors, which are present in immune-responsive cells like macrophages or specialized cells of the intestinal mucosa. These interactions would facilitate targeting of the naturally encapsulated active agents of the present invention to the effector cells in the intestinal mucosa.

Other aspects and advantages of the present invention will be more fully apparent from the detailed description below.

DISCLOSURE OF INVENTION

In an aspect of the present invention the active agents are peptides expressed fused to sequences that promotes attachment to lipid droplets or lipid membranes in general. The majority of eukaryotic cells synthesize neutral lipids and package them into cytosolic lipid droplets. In vertebrates, triacylglycerol-rich lipid droplets of adipocytes provide a major energy storage depot for the body, whereas cholesteryl ester-rich droplets of many other cells provide building materials for local membrane synthesis and repair. These lipid droplets are coated with one or more of five members of the perilipin family of proteins (PAT family): adipophilin, TIP47, OXPAT/MLDP, S3-12, and perilipin BRASAEMBLE, D. L., et al. Thematic review series: adipocyte biology. The perilipin family of structural lipid droplet proteins: stabilization of lipid droplets and control of lipolysis. *J. Lipid. Res.* 2007, vol. 48, no. 12, p. 2547-59.

The PAT family was originally identified through homology to a highly conserved 100 amino acid domain in the amino terminus of perilipin, the "PAT domain" (FIG. 1).

In a preferred embodiment of the present invention the sequence that promotes attachment of the fusion peptide to lipid membranes derives from a protein of the PAT family or homologues thereof BICKEL, P. E., et al. PAT proteins, an ancient family of lipid droplet proteins that regulate cellular lipid stores. *Biochim. Biophys. Acta.* 2007, vol. 1791, no. 6, p. 419-40. In a more preferred embodiment of the present invention said sequence derives from an insect express PAT protein or homologues thereof.

Insects express PAT proteins are categorized into two distinct subfamilies (LSD-1 and LSD-2; lipid storage droplet protein-1 and -2) (FIG. 1). Emerging evidence suggests that—like mammalian family members—insect PATs can play crucial roles in PKA-triggered lipolysis and promote storage of neutral lipids. Many other features are shared with mammalian PATs: they localize to lipid droplets, they are regulated by phosphorylation (with PKA one of the responsible kinases), and they work together with the ATGL/Brummer family of lipases GRÖNKE, S., et al. Control of fat storage by a Drosophila PAT domain protein. *Curr. Biol.* 2003, vol. 13, no. 7, p. 603-6.

It is believed that PAT proteins anchor onto lipid droplets through several hydrophobic domains (FIG. 1), which embed into the neutral lipid-filled core, whereas a central highly charged acidic domain loops away from the surface of the lipid droplet. The sequences with the characteristics of amphipathic β-pleated sheets may be shallowly embedded into the surface phospholipids of the droplets GARCIA, A., et al. The central domain is required to target and anchor perilipin A to lipid droplets. *J. Biol. Chem.* 2003, vol. 278, no. 1, p. 625-35.

In a preferred embodiment of the present invention the sequence used to promote attachment of the fusion peptide to lipid membranes includes the lipid droplet targeting helices of the LSD1 protein of the silkworm *Bombyx mori* (SEQ ID NO:1).

In another embodiment of the present invention the sequence that promotes attachment of the fusion peptide to lipid membranes derives from the human caveolin protein family or homologues thereof GLENNEY, J. R., et al. Sequence and expression of caveolin, a protein component of caveolae plasma membrane domains phosphorylated on tyrosine in Rous sarcoma virus-transformed fibroblasts. *Proc. Natl. Acad. Sci. USA.* 1992, vol. 89, no. 21, p. 10517-21.

Caveolae are small invaginations of the plasma membrane, and are assumed to play important roles in signal transduction, cholesterol transport, and endocytosis. Caveolins are essential for the above functions and form the structural framework of caveolae FUJIMOTO, T., et al. Caveolin-2 is targeted to lipid droplets, a new "membrane domain" in the cell. *J. Cell Biol.* 2001, vol. 152, no. 5, p. 1079-85. Caveolin-2, especially its β-isoform, is targeted to the surface of lipid droplets. The central hydrophobic domain of caveolin-2 (residues 87-119) and the N-terminal (residues 70-86) and C-terminal (residues 120-150) hydrophilic domains are all necessary for the localization in lipid droplets. The N- and C-terminal domains appear to be related to membrane binding and exit from ER, respectively, implying that caveolin-2 is synthesized and transported to lipid droplets as a membrane protein.

In a specific aspect of the present invention, the fusion peptide contains the N- and C-termini of the β-isoform of human caveolin 2 and a hydrophobic central domain (SEQ ID NO: 2). In another specific aspect of the present invention, the fusion peptide contains N-terminus of the β-isoform of human caveolin 2, a hydrophobic central domain and a ER-retention signal at the C-terminus (SEQ ID NO: 3).

In another embodiment of the present invention the sequence that promotes attachment of the fusion peptide to lipid membranes derives from the protein family of the Ancient ubiquitous protein 1 (AUP1) or homologues thereof.

Quality control of endoplasmic reticulum proteins involves the identification and engagement of misfolded proteins, dislocation of the misfolded protein across the ER membrane, and ubiquitin-mediated targeting to the proteasome for degradation. AUP1 physically associates with the mammalian HRD1/SEI1L complex and AUP1-depletion impairs degradation of misfolded ER proteins. One of the functions of AUP1 in ER quality control is to recruit the soluble E2-ubiquitin conjugating enzyme UBE2G2. The CUE domain of AUP1 regulates polyubiquitylation and determines AUP1's interaction with the HRD1 complex and dislocation substrates (FIG. 2).

AUP1 localizes both to the ER and to lipid droplets. AUP1 expression level affects the abundance of cellular lipid droplets and as such represents the first protein with lipid droplet regulatory activity to be linked to ER quality control KLEMM, E. J., et al. Dual role of ancient ubiquitous protein 1 (AUP1) in lipid droplet accumulation and endoplasmic reticulum (ER) protein quality control. *J. Biol. Chem.* 2011, vol. 286, no. 43, p. 37602-14. AUP1 contains a hydrophobic region close to the N-terminus (FIG. 2) that inserts into the membrane such that both termini are found in the cytoplasm SPANDL, J., et al. Ancient ubiquitous protein 1 (AUP1) localizes to lipid droplets and binds the E2 ubiquitin conjugase G2 (Ube2g2) via its G2 binding region. *J. Biol. Chem.* 2011, vol. 286, no. 7, p. 5599-5606.

In a preferred embodiment of the present invention the sequence used to promote attachment of the fusion peptide to lipid membranes includes the lipid droplet targeting hydrophobic region of the AUP1 protein of the bee *Apis mellifera* (SEQ ID NO:4).

The insect fat body is functionally similar to mammalian liver. It contains a single cell type which synthesizes, stores, and mobilizes glycogen, lipid, and proteins. The fat body is a relatively large organ distributed throughout the insect body, preferentially underneath the integument and surrounding the gut and reproductive organ. The basic cell of the fat body is the adipocyte, characterized by the presence of numerous lipid droplets ARRESE, E L., et al. Insect fat body: energy, metabolism, and regulation. *Annu. Rev. Entomol.* 2010, no. 55, p. 207-25.

In another embodiment of the present invention, the product of interest is accumulated into the insect fat body adipocytes when said product of interest is linked to any of the lipid membrane targeting sequences commented above.

Methods of purification of the lipidic intracellular vesicles of fat bodies have been previously described. In a further embodiment of the present invention, the product of interest accumulated in the insect fat body is purified by applying a method of purification of said intracellular vesicles, wherein said method might be based on, but it is not restricted to, density gradient purification.

In yet another embodiment of the present invention the sequence that promotes what can be defined as an amphipathic helical conformations, which is able to self-assemble and which has a tendency to impart orientational organization to supramolecular structures is also defined. Said sequence (see SEQ ID NO: 5) being capable of self-assembly; similar polyproline sequences were defined by Lee et al. LEE, K. K., et al. Site-selective intramolecular hydrogen-bonding interactions in phosphorylated serine and threonine dipeptides. *J. Phys. Chem. B.* 2008, vol. 112, no. 51, p. 16782-87. as being capable of aggregating to form supramolecular nanostructures, in fact the molecule defined by Lee et al. was capable of forming a hollow sphere.

Serendipitously, the fusion product forms an organized nanostructure when an active polypeptide is fused to the polyproline sequence defined in the patent.

A further embodiment of this particular invention is the use of density isolation techniques to isolate/enrich the nanostructures; also the sequence itself lends itself to purification via immobilized metal affinity techniques due to the His residues in the sequence which upon formation of the polyproline structure is pushed in close proximity to each other.

EXAMPLES

Example 1

Figure 1:
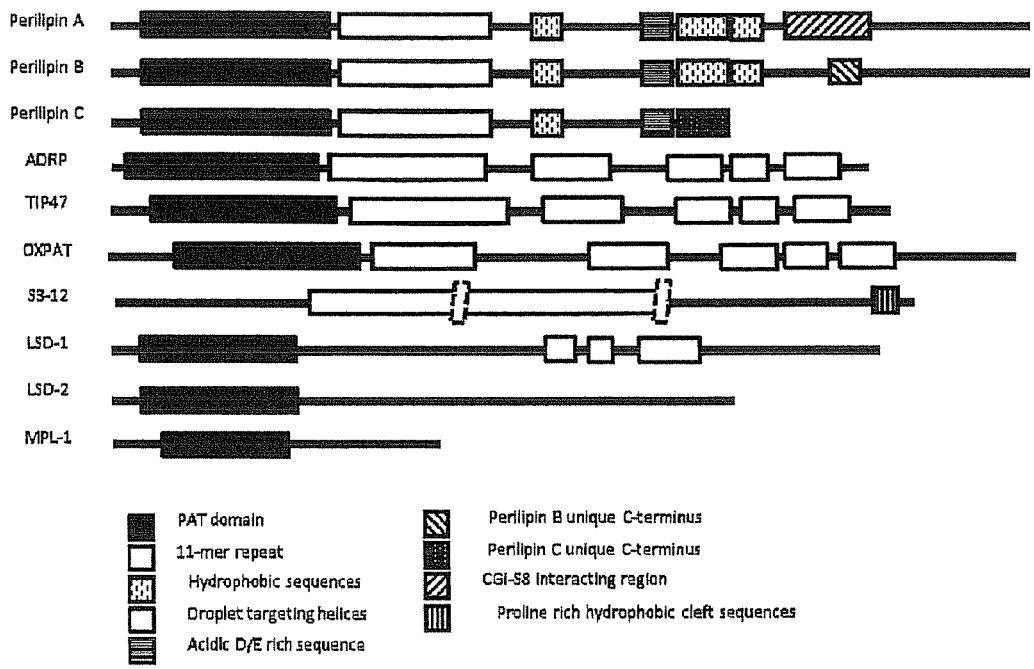
FIG. 1. Structure of ten members of the PAT family of lipid droplet proteins. The first seven shown (perilipin A through S3-12) are from mammals, the last three from non-mammalian species (flies and fungi, respectively). These proteins share an approx. 100 amino acid region of high sequence similarity near their N-termini (PAT domain). Information based on Bickel et al.
Figure 2:
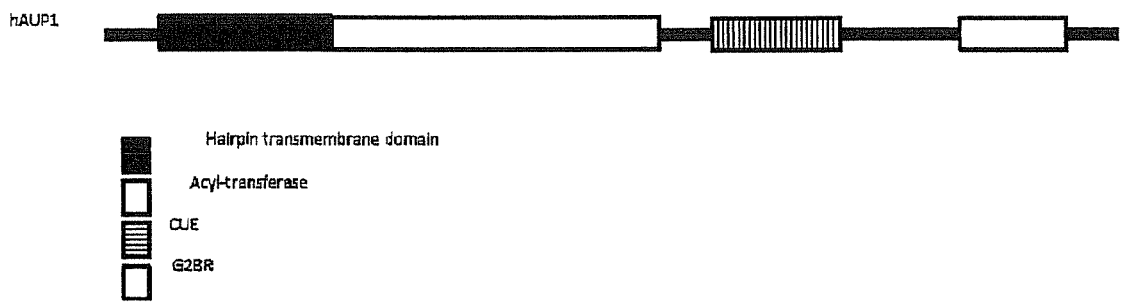
FIG. 2. Domain structure of the AUP1 protein family. AUP1 has 410 amino acids and is highly conserved among multicellular organisms. The figure (human AUP1) shows the four conserved domains. The N-terminal hairpin transmembrane domain is the one used to target antigens to lipid droplets in the present invention.

Oral Vaccination of Rainbow Trout Against IHNV

Separate batches of *Trichoplusia ni* larvae were infected with (a) a recombinant baculovirus expressing the glycoprotein G and nucleoprotein N of the infectious necrosis hematopoietic virus (IHNV); (b) a recombinant baculovirus expressing fusion proteins consisting in the sequences of glycoprotein G and nucleoprotein N of IHNV fused to the lipid droplet targeting sequence of *Bombyx mori* Lsd1 protein; (c) a recombinant baculovirus expressing fusion proteins consisting in the sequences of glycoprotein G and nucleoprotein N of IHNV fused to a polyproline sequence; and (d) control baculovirus with an empty vector.

The infected larvae were harvested at 80 hours postinfection and frozen. Oral vaccines were prepared by mixing 1.5 g of homogenized larvae with 3 g of fish oil. The oily mixture was used to coat 100 g of standard commercial feed for rainbow trout juveniles. Thirty rainbow trout fry with an average body weight of 0.12 g were held in 1.5-L polypropylene tanks and used for the study. In each experiment, fish were vaccinated by feeding them with oral vaccines prepared as described above with the different batches of infected larvae and a control prepared by using uninfected larvae for coating the food.

The immune response of vaccinated fish was measured by (a) real-time quantitative PCR analysis of expression of genes related with the innate and adaptive immune response (immunoglobulins, IFN-γ1, IFN-γ2, gig2, mhc2b, mhc1, mxb, and mxc) and (b) ELISA by coating plates with vaccinated fish sera, capturing purified IHNV-G and -N proteins, and detecting with specific secondary antibodies. Vaccinated animals developed a specific immune response with production anti-IHNV antibodies over two months following vaccination.

The invention claimed is:

1. A formulation for delivery of a pharmaceutically active agent to an animal or human comprising:
 a heterologous peptide, wherein said heterologous peptide comprises a first peptide sequence and a second peptide sequence,
 wherein said first peptide sequence is linked to said second peptide sequence,
 wherein said first peptide sequence promotes the fusion of said second peptide sequence to lipid membranes, and
 wherein said first peptide sequence is a lipid-droplet targeting sequence comprising SEQ ID NO:1.

2. The formulation according to claim 1, wherein said second peptide sequence is selected from the group consisting of immunogenic peptides and glycopeptides, wherein said immunogenic peptides and glycopeptides are able to induce an immune response against pathogens in an animal or human.

3. The formulation according to claim 1, wherein said second peptide sequence is a bioactive peptide or a glycopeptide that is able to induce a prophylactic or therapeutic effect on an animal or human condition.

4. A method of preparing the formulation according to claim 1, comprising:
 growing host cells or host organisms under conditions that allow expression of the heterologous peptide;
 harvesting said host cells or host organisms, or taking a sample from a culture media used for growing said host cells or taking a sample from said host organism; and
 preparing a clarified homogenate or crude extract.

5. The method according to claim 4, wherein the host cells or host organisms are insect cells, insect larvae or insect pupae.

6. The method according to claim 4, comprising infecting the host cells or host organisms with a recombinant baculovirus; and expressing the heterologous peptide.

7. The method according to claim 5, wherein the host organisms are insect larvae of a species selected from the group consisting of *Trichoplusia ni*, *Spodoptera frugiperda*, *Spodoptera exigua*, *Autographa gamma*, *Peridroma saucia*, *Noctua pronuba*, *Aporophyla nigra*, *Hoplodrina ambigua*, *Xestia xantographa*, *Agrotis puta*, and *Agrotis segetum*.

8. A method for eliciting an immunological response in an animal or human comprising administering to the animal or human the formulation prepared according to claim 4.

9. A method for delivery of a pharmaceutically active agent to an animal or human comprising administering to the animal or human the formulation prepared according to claim 4.

* * * * *

SEQUENCE LISTING

```
<160> NUMBER OF SEQ ID NOS: 5

<210> SEQ ID NO 1
<211> LENGTH: 109
<212> TYPE: PRT
<213> ORGANISM: Bombyx mori
<220> FEATURE:
<221> NAME/KEY: SOURCE
<222> LOCATION: 1..109
<223> OTHER INFORMATION: /mol_type="protein"
      /organism="Bombyx mori"

<400> SEQUENCE: 1

His Gly Ala Arg Phe Lys Arg Lys Leu Gln Arg Arg Leu Thr Arg Gln
1               5                   10                  15

Ala Leu Ala Glu Ala Lys Ala Ile Lys Glu Gln Ile His Val Leu Val
            20                  25                  30

Tyr Val Ala Glu Leu Val Ala Lys Asp Pro Val Leu Ala Trp Lys Lys
        35                  40                  45

Ala Lys Glu Leu Tyr Ala Ser Leu Ser Gln Pro Glu Pro Glu Asn Gln
    50                  55                  60

Ala Arg Pro Val Thr Leu Glu Glu Leu Met Val Leu Leu Thr Arg Glu
65                  70                  75                  80

Thr Ala Arg Lys Val Val His Leu Val Asn Tyr Thr His Thr Asp Leu
                85                  90                  95

Pro Arg Asn Ile Arg Gln Gly Met Ser Ile Val Tyr Lys
            100                 105

<210> SEQ ID NO 2
<211> LENGTH: 72
<212> TYPE: PRT
<213> ORGANISM: artificial sequences
<220> FEATURE:
<221> NAME/KEY: SOURCE
<222> LOCATION: 1..72
```

```
<223> OTHER INFORMATION: /mol_type="protein"
      /note="Human caveolin-2 derived sequence"
      /organism="artificial sequences"

<400> SEQUENCE: 2

Trp Ile Cys Ser His Ala Leu Phe Glu Ile Ser Lys Tyr Val Met Tyr
1               5                   10                  15

Lys Leu Leu Val Leu Leu Val Leu Val Leu Leu Val Leu Leu Val
            20                  25                  30

Leu Leu Val Leu Leu Val Leu Leu Val Lys Thr Cys Leu Met Val Leu
            35                  40                  45

Pro Ser Val Gln Thr Ile Trp Lys Ser Val Thr Asp Val Ile Ile Ala
50                  55                  60

Pro Leu Cys Thr Ser Val Gly Arg
65                  70

<210> SEQ ID NO 3
<211> LENGTH: 45
<212> TYPE: PRT
<213> ORGANISM: artificial sequences
<220> FEATURE:
<221> NAME/KEY: SOURCE
<222> LOCATION: 1..45
<223> OTHER INFORMATION: /mol_type="protein"
      /note="Human caveolin-2 derived sequence"
      /organism="artificial sequences"

<400> SEQUENCE: 3

Trp Ile Cys Ser His Ala Leu Phe Glu Ile Ser Lys Tyr Val Met Tyr
1               5                   10                  15

Lys Leu Leu Val Leu Leu Val Leu Val Leu Leu Val Leu Leu Val
            20                  25                  30

Leu Leu Val Leu Leu Val Leu Leu Val Lys Asp Glu Leu
            35                  40                  45

<210> SEQ ID NO 4
<211> LENGTH: 87
<212> TYPE: PRT
<213> ORGANISM: Apis
<220> FEATURE:
<221> NAME/KEY: SOURCE
<222> LOCATION: 1..87
<223> OTHER INFORMATION: /mol_type="protein"
      /organism="Apis"

<400> SEQUENCE: 4

Ile Asp Ile Gln Asp Leu Phe Asp Lys Ser Arg Phe Pro Ser Gly Trp
1               5                   10                  15

Arg Leu Ile Phe Ile Phe Leu Tyr Thr Pro Val Gly Ile Leu Leu Val
            20                  25                  30

Leu Leu Arg Leu Leu Ile Ala Leu Gln Leu Trp Leu Val Ala Ile Leu
            35                  40                  45

Leu Pro Asp Cys Asn Ile Leu Arg Thr Phe Leu Ser His Gly Phe Ser
50                  55                  60

Phe Ala Phe Gly Ile Leu Val Lys Ile Pro Glu Gly Glu Val Lys Asp
65                  70                  75                  80

Lys Gln Ser Arg Ile Ile Ile
                85

<210> SEQ ID NO 5
<211> LENGTH: 28
<212> TYPE: PRT
```

```
<213> ORGANISM: artificial sequences
<220> FEATURE:
<221> NAME/KEY: SOURCE
<222> LOCATION: 1..28
<223> OTHER INFORMATION: /mol_type="protein"
      /note="Polyproline sequence"
      /organism="artificial sequences"

<400> SEQUENCE: 5

Pro Val His Pro Pro His His Pro Val His Pro Pro His His Pro Val
1               5                   10                  15

His Pro Pro His His Pro Val His Pro Pro His His
            20                  25
```